United States Patent
Desrosiers et al.

(10) Patent No.: US 6,667,009 B1
(45) Date of Patent: Dec. 23, 2003

(54) APPARATUS FOR SAMPLING AND ANALYSIS OF REACTIONS BY TRAPPING REACTION COMPONENTS ON A SORBENT

(75) Inventors: Peter J. Desrosiers, Cupertino, CA (US); Christopher E. Dubé, San Jose, CA (US); Xiao Ping Zhou, Sunnyvale, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/553,244

(22) Filed: Apr. 20, 2000

Related U.S. Application Data (62) Division of application No. 09/149,586, filed on Sep. 8, 1998.

(51) Int. Cl.[7] ............................ B01L 11/00; B01J 19/00
(52) U.S. Cl. .................. 422/101; 422/68.1; 422/99; 422/102; 422/129; 422/131; 436/37; 436/174; 436/177; 436/178
(58) Field of Search ................. 422/68.1, 62, 99, 422/101, 102, 104, 129, 130, 131; 436/37, 174, 178, 177

(56) References Cited

U.S. PATENT DOCUMENTS

| | | | |
|---|---|---|---|
| 3,431,077 A | | 3/1969 | Danforth |
| 4,135,908 A | * | 1/1979 | Widmer ............................ 71/9 |
| 4,483,925 A | | 11/1984 | Noack ........................ 435/293 |
| 5,011,779 A | | 4/1991 | Maimon |
| 5,516,490 A | | 5/1996 | Sanadi ........................ 422/101 |
| 5,741,463 A | | 4/1998 | Sanadi ........................ 422/101 |
| 5,770,860 A | | 6/1998 | Franzen ...................... 250/288 |
| 5,866,342 A | | 2/1999 | Antonenko et al. |
| 5,872,010 A | | 2/1999 | Karger et al. |
| 5,888,830 A | | 3/1999 | Mohan et al. |
| 5,959,297 A | * | 9/1999 | Weinberg et al. ........... 250/288 |
| 5,976,813 A | | 11/1999 | Beutal et al. |
| 5,985,356 A | * | 11/1999 | Schultz et al. .................. 427/8 |
| 6,004,617 A | * | 12/1999 | Schultz et al. .................. 427/8 |
| 6,034,775 A | | 3/2000 | McFarland et al. |
| 6,190,619 B1 | * | 2/2001 | Kilcoin et al. .............. 422/131 |
| 6,326,090 B1 | * | 12/2001 | Schultz et al. .............. 428/688 |
| 6,346,290 B1 | * | 2/2002 | Schultz et al. .................. 427/8 |
| 6,508,984 B1 | * | 1/2003 | Turner et al. .................. 422/65 |
| 6,537,500 B1 | | 3/2003 | Brenner et al. ................ 422/88 |

FOREIGN PATENT DOCUMENTS

| | | | |
|---|---|---|---|
| EP | 0 971 225 | 1/2000 | .......... G01N/21/17 |
| WO | 96/11878 | 4/1996 | |
| WO | 97/32208 | 4/1997 | |
| WO | 98/03521 | 1/1998 | |
| WO | WO 98/15969 | 4/1998 | ............ H01J/49/00 |
| WO | WO 98/56796 | 12/1998 | ............ C07F/19/00 |
| WO | WO 99/05318 | 2/1999 | ............ C12Q/1/68 |

OTHER PUBLICATIONS

V. Toome et al., *Preliminary Evaluation of Fluorescamine as a Colorimetric Reagent for Primary Amines*, Analytical Letters, 7(6), pp. 437–443, 1974.

(List continued on next page.)

*Primary Examiner*—Jill Warden
*Assistant Examiner*—Dwayne K Handy

(57) ABSTRACT

Methods and devices for rapidly analyzing groups of reactions are disclosed. The method includes the steps of contacting a fluid sample from one of the reaction mixtures with a sorbent, trapping at least one component of the fluid sample on the sorbent, and detecting the at least one component of the fluid sample trapped on the sorbent. The contacting step, the trapping step, and the detecting step are carried out at least once for each of the reaction mixtures in rapid serial or parallel fashion. The present invention is useful for screening combinatorial libraries, especially libraries of catalysts made through parallel synthesis, but the disclosed methods and devices can be used to analyze a broad spectrum of chemical transformations.

33 Claims, 8 Drawing Sheets

OTHER PUBLICATIONS

V. Toome, *A Simple Simultaneous Colrimetric Determination of Primary and Secondary Amines with* Fluorescamine, Analytical Letters, 8(7), pp. 441–448, 1975.

W. Henry Weinberg, et al., *Combinatorial Methods in Homogeneous and Heterogeneous Catalysis*, Current Opinion in Solid State & Materials Science, 3, pp. 104–110, 1998.

A.M. Felix et al., *Usage of Flourescamine as a Spray Reagent for Thin–Layer Chromatography*, Journal of Chromatography, 89, pp. 361–364, 1974.

A.H.M.T Scholten et al., *Flouorescence Detection of Chloroanilines Liquid Chromatography Using a* Post–Column Reaction with Fluorescamine, Journal of Chromatogrophy, 218, pp. 3–13, 1981.

A.V. Belyaeva, *Use of GVV–1Gas Detector for Rapid Analysis of Mine Air*, (Abstract) Ugol'Ukr., pp40–41, Issue 3 (1996).

B.A. Tomkins et. al., *Derivitization of Primary AromaticAmines with Fluorescamine*, Analytical Letters, 13 (A7), pp. 589–602, 1980.

F.C. Moates, et al., *Infrared Thermographic Screening of Combinatorial Libraries of Heterogeneous* Catalysts, Ind. Eng. Chem. Res., 35, pp. 4801–4803, 1996.

Hellmut Jork, et al., *Thin–Layer Chromatography: Reagents and Detection Methods*, vol. La, Editor: Ebel, H.F., Publisher: VCH, New York, ISBN 0–89573–876–7, pp. 55–118, 1990.

Hellmut Jork, et al., *Thin–Layer Chromatography: Reagents and Detection Methods*, vol. La. Editor: Dyllick–Brezinger: C., Sora, K., Publisher: VCH, New York, ISBN 1–56081–109–X, pp. 3–139, 1994.

I.F. Mao, et al., *Simultaneous Determination of Urinary Metabolites of Toluene, Xylene, Styrene and Ethyl Benzene by Solid–Phase Extraction Technique and High–Performance Liquid Chromatographic/Photo Diode Array Detection*, International Journal of Environmental Analytical Chemistry, 64, pp. 1–9, 1996.

J. Bartos et al., *Spectrophotometric and Fluorimetric Determination of Amines*, Pure & Appl. Chem., 56–4, pp. 467–477, 1984.

J. Sherma et al., *Detection and Quantitation of Anilines by TLC Using Fluroscamine Reagent*, American Laboratory, pp. 21–31, Oct. 1974.

Posner B. et al., "Catalytic Antibodies: Perusing Combinatorial Libraries" TIBS Trends in Biochemical Sciences, Apr. 1994, vol. 19, pp. 145 to 150, ISSN 098–0004.

J.C. Young, *Fluorescence Method for Detecting Aldehydes at Picomole Level on Thin–Layer* Chromatographic Plates, Journal of Chromatography, 130, pp. 392–395, 1997.

J.H. Richardson, *Sensitive Assay of Biochemicals by Laser–Induced Molecular Fluorescence*, Analytical Biochemistry, 83, pp. 754–762, 1977.

Justus, G. Kirchner, *Thin Layer Chromatography: Detection of Colorless Compounds*, John Wiley, pp. 198–253, ISBN 0–471–93264–7, 1978.

K. G. Krebs, et al., *Thin–Layer Chromatography: Z. Spray Reagents*, Editor: Stahl, E., Springer–Verlag, pp. 854–909, 1969.

Kevin Burgess, et al., *New Catalysts and Conditions for a C–H Insertion Reaction Identified by High* Throughput Catalyst Screening, Agnew. Chem. Int. Ed. Engl., 35/2, pp. 220–222, 1996.

Matthew B. Francis, et al., *Combinatorial Approach to the Discovery of Novel Coordination* Complexes, J. Am. Chem. Soc., 118, pp. 8983–8984, 1996.

Merck Web Page, HPTLC Layers with Spherical Silica Gels, www.merck.de/chromatography/tlc/tlcspher.htm, Apr. 21, 1998.

Merck Web Page, Sorbents for HPLC, http://www.merck.de/chromatography/hplc/sorbents.htm, Apr. 21, 1998.

S. De Bernardo et al., *Studies on the Reaction of Fluorescamine with Primary Amines, Archives of* Biochemistry and Biophysics, 163, pp. 390–399, 1974.

Supelco Corporation, *Analysis of Stack Emissions Using VOST Air Sampling Tubes and Capillary GC*, Application Note 104, 1996.

Supelco Corporation, *Carbon Layer Open Tubular Columns for Capillary GC Analyses of Volatile* Compounds, Application Note 35, 1994.

Supelco Corporation, *ENVI™–18 SPE Tube Ensures Low Background for Monitoring Organic* Compounds in Drinking Water by EPAA Method 525, Application Note 65, 1996.

Supelco Corporation, *Extract Nonvolatile Pesticides from Drinking Water, Using a Graphitized Carbon* Adsorbent, Application Note 27, 1994.

Supelco Corporation, *Fast Screening for Chlorinated Pesticides by Solid Phase* MicroExtraction/Capillary GC, Application Note 58, 1995.

Supelco Corporation, *High–Purity Ion Pair Reagents for Acidic and Basic Compounds*, product specification, 1996.

Supelco Corporation, *Monitor Organophosphorous Pesticides in Air, Using ORBO™–49P Tubes and* Capillary GC, Application Note 33, 1994.

Supelco Corporation, *Solid Phase Microextraction/Capillary GC: Rapid, Sensitive Detection of* Gasoline in Fire Debris, Application Note 61, 1997.

Supelco Corporation, *SPB–50 Capillary Column for Environmental Application*, Application Note 49, 1995.

Supelco Corporation, *Supelcarb™ GC Split Vent Traps Adsorb Toxic Compounds Longer Than* Conventional Traps, Application Note 96, 1995.

Supelco Corporation, Supelco LC Media Selection Guide, Bulletin 881C, 1997.

Supelco Corporation, Superclean™ Solid Phase Extraction Tubes, product specification, 1997.

Supelco Corporation, *Thermal Desorption Applications Guide for Model 890/891 Thermal Desorption* Unit and Dynamic Thermal Stripper, Bulletin 873A, 1996.

Supelco Corporation, *Use Solid Phase Extraction to Isolate Phenols from Aqueous Samples*, Application Note 32, 1996.

* cited by examiner

APPARATUS FOR SAMPLING AND ANALYSIS OF REACTIONS BY TRAPPING REACTION COMPONENTS ON A SORBENT

This application is a divisional application of U.S. patent application Ser. No. 09/149,586 filed Sep. 8, 1998 by Desoriers et al.

BACKGROUND OF THE INVENTION

1. Technical Field

The present invention relates to a method and apparatus for analyzing reaction mixtures, and relates more particularly, to a method and apparatus for screening combinatorial libraries.

2. Discussion

Combinatorial chemistry refers generally to methods for rapidly creating collections of compounds having diverse structures and to methods for rapidly testing or screening chemical libraries to discover or optimize compounds or materials exhibiting desired properties.

Combinatorial chemistry is an effective research strategy for discovering useful materials. For example, pharmaceutical scientists have successfully used such techniques to dramatically increase the speed of drug discovery. Material scientists have employed combinatorial methods to develop novel high temperature superconductors, magnetoresistive materials, and phosphors. More recently, scientists have applied combinatorial methods to develop catalysts. See, for example, co-pending U.S. patent application Ser. No. 08/327,513 "The Combinatorial Synthesis of Novel Materials" (published as WO 96/11878) and co-pending U.S. patent application Ser. No. 08/898,715 "Combinatorial Synthesis and Analysis of Organometallic Compounds and Catalysts" (published as WO 98/03521), which are both herein incorporated by reference.

Combinatorial libraries may consist of elements or compounds, e.g., individual library members, that are synthesized or mixed in separate vessels, or arrayed on planar solid supports (wafers) frequently using automated dispensing instruments. Each vessel or wafer array position is provided with a starting reactant, which is treated with different reactants. The treating step can be repeated many times with different sets of reagents resulting in a diverse combinatorial library.

Though when compared to traditional approaches, new and useful materials can be developed in less time using combinatorial methods, further efficiency gains can be achieved by improving library screening. Once a researcher creates a combinatorial library, he or she faces the daunting task of identifying a handful of promising materials out of a combinatorial library comprising hundreds, thousands or perhaps millions of compounds. Generally, the speed at which one may screen libraries for useful properties has not kept pace with the speed at which libraries can be created.

Furthermore, screening library members for catalytic activity presents unique problems. For example, screening methods developed for solid phase catalysts are often unsuitable for use with solution phase catalysts. Furthermore, many screening methods developed for solution-phase catalysts, which rely on quantifying the amount of a desired product formed by contacting reactants with the catalysts, require time consuming separations, because the reactants and catalysts may interfere with detection of the desired product.

The present invention is directed to overcoming, or at least minimizing, one or more of the problems set forth above.

SUMMARY OF THE INVENTION

The present invention helps solve many of the problems associated with screening combinatorial libraries. Indeed, the present invention provides methods and devices for parallel or rapid serial screening of libraries made through parallel synthesis. Furthermore, the inventive methods are flexible techniques that can be used to screen both solid phase and solution phase catalysts, and they do not require elaborate procedures for separating reactants, products, and catalysts prior to screening. Although the present invention is especially well suited for screening combinatorial libraries, the inventive method and apparatus can be used to analyze a broad range of chemical transformations.

Thus, in accordance with a first aspect of the present invention, there is provided a method of analyzing reaction mixtures. The method comprises the steps of contacting a fluid sample from one of the reaction mixtures with a sorbent, trapping at least one component of the fluid sample on the sorbent, and detecting the at least one component of the fluid sample trapped on the sorbent. The contacting step, the trapping step, and the detecting step are carried out at least once for each of the reaction mixtures.

In accordance with a second aspect of the present invention, there is provided a method of screening a group of catalysts. The method comprises the steps of combining each of the catalysts with at least one reactant so as to form a plurality of reaction mixtures. The method further comprises contacting a fluid sample from one of the reaction mixtures with a sorbent, trapping at least one component of the fluid sample on the sorbent, and detecting the at least one component of the fluid sample on the sorbent. The contacting step, the trapping step, and the detecting step are carried out at least once for each of the reaction mixtures.

In accordance with a third aspect of the present invention, there is provided an apparatus for analyzing reaction mixtures. The apparatus comprises a reaction block having wells formed along an upper surface, and a sorbent layer disposed above the upper surface of the reaction block such that the wells and the sorbent layer define vessels for containing the reaction mixtures. The sorbent layer is adapted to trap at least one fluid component of the reaction mixtures.

In accordance with a fourth aspect of the present invention, there is provided an apparatus for analyzing reaction mixtures comprising vessels for containing each of the reaction mixtures, and discrete sorbent traps that are in fluid communication with the vessels. The sorbent traps are adapted to trap at least one fluid component of the reaction mixtures.

In accordance with a fifth aspect of the present invention, there is provided an apparatus for screening reaction mixtures in which at least one constituent of the reaction mixtures is contained in depressions located along a top surface of a planar substrate. The apparatus comprises a heating block that is adapted to support the planar substrate and to provide thermal contact with a bottom surface of the planar substrate. The apparatus includes a gas permeable sorbent layer having an upper surface and a lower surface, in which the lower surface of the sorbent layer is disposed above the top surface of the planar substrate. The sorbent layer is adapted to trap at least one vapor phase component of the reaction mixtures. The apparatus further comprise a cover having an upper surface and a lower surface, the lower surface of the reactor cover disposed above the upper surface of the sorbent layer. Passageways are formed in the cover that extend from the lower to the upper surfaces of the cover and provide flow paths for vapor phase components of the reaction mixtures from the upper surface of the cover to the at least one constituent of the reactive mixture.

DETAILED DESCRIPTION OF THE PREFERRED EMBODIMENTS

The present invention provides a method and apparatus for rapidly analyzing reactions. Although one may use the invention to examine a broad range of gas and liquid-phase reactions, it is especially useful for screening combinatorial libraries. As described below, an important application includes distinguishing library members based on their ability to catalyze a particular reaction.

Figure 1:
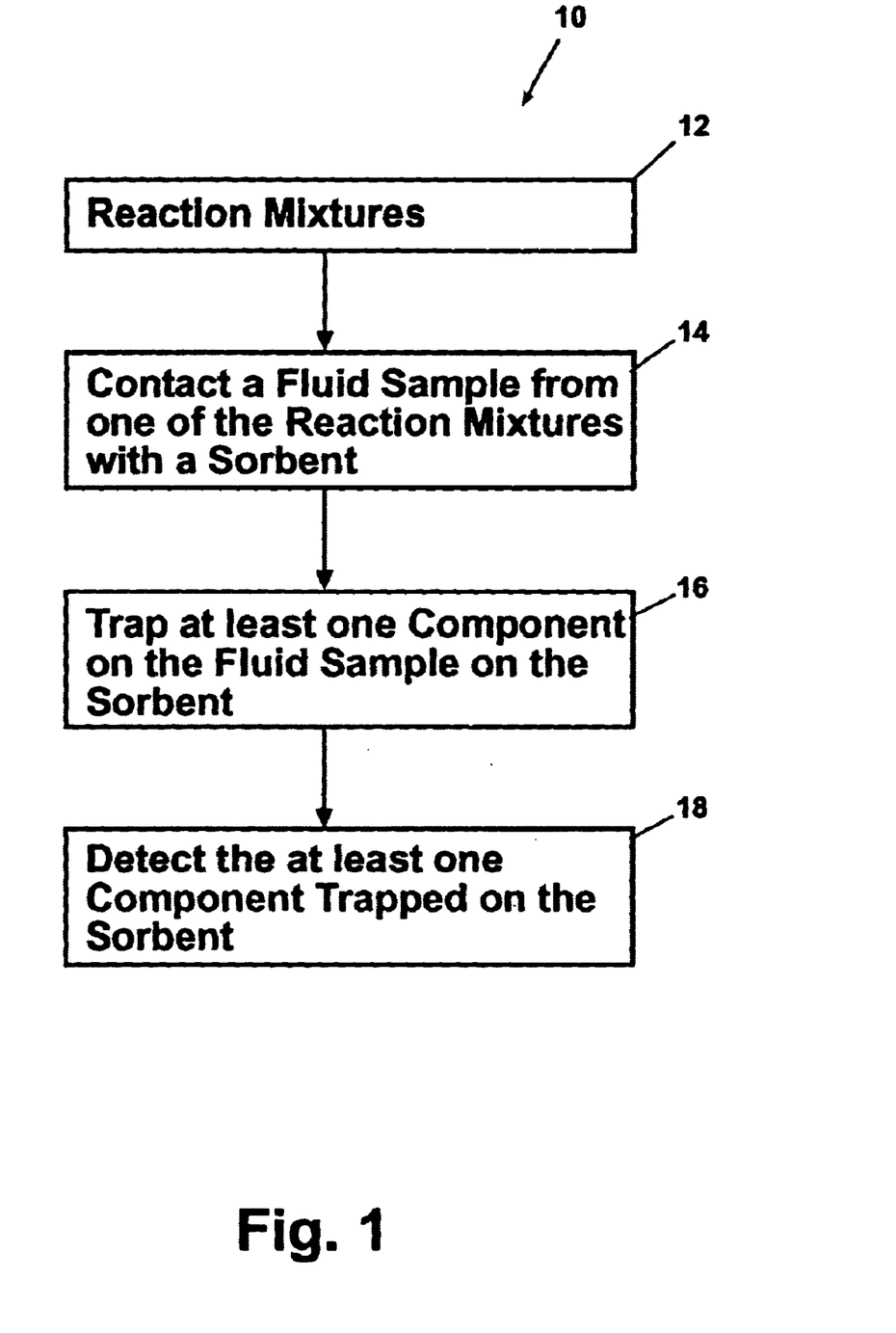
FIG. 1 is a flow chart illustrating the general features of the disclosed method.

FIG. 1 illustrates general features of the method 10 for analyzing reaction mixtures 12. The method comprises the steps of contacting 14 a fluid sample from one of the reaction mixtures 12 with a sorbent, followed by trapping 16 at least one component of the fluid sample on the sorbent, and detecting 18 the trapped component or components. The fluid sample can be a liquid or a gas or a mixture of a gas and a liquid. Each of the reaction mixtures 12 can include, but is not limited to reactants, products, solvents, catalysts and activators. Typically, the trapped component is a reaction product, but it can be any fluid component of the reaction mixture, including a reactant. To speed analysis, the contacting 14 step or the detecting 18 step or both can be carried out for two or more of the reaction mixtures 12 simultaneously (that is, in parallel). Normally, fluid samples from each of the reaction mixtures 12 are in contact with the sorbents for the same amount time.

Sorbent contacting 14 can occur through many methods. For example, after loading reaction mixtures 12 in vessels, individual sorbent traps can be placed in the headspace of each of the vessels, so that during reaction the vapor phase of each of the reaction mixtures contacts the sorbent. Alternatively, the sorbent traps may be located outside of the vessels, but in fluid communication with the headspace of the vessels via conduits. In either case, if the reaction mixtures comprise a liquid phase and a vapor phase, the fraction of the component of interest in the vapor phase is generally different than the fraction of the same component in the liquid phase.

Instead of individual traps, the sorbent may consist of a thin layer of sorbent. In such cases, the reaction mixtures 12 can be placed in vessels formed in a surface of a reaction block. One may then place the layer of sorbent on the surface of the reaction block so that vapor from each of the reaction mixtures contacts discrete areas of the sorbent layer during or following reaction. The sorbent layer may be disposed on a solid substrate, e.g., thin layer chromatography (TLC) plate, and may be discontinuous to help prevent component migration from one of the discrete contacting areas to another. Furthermore, the solid substrate can be gas permeable, allowing vapor from each of the reaction mixtures to pass through the sorbent layer. The gas permeable substrate is useful when analyzing gas-phase reactions—one may charge (pressurize) each of the vessels with one or more gaseous reactants, and then vent the mixture through the sorbent layer following reaction, trapping the desired component.

When the fluid samples are liquids, one may use standard liquid transfer techniques for sorbent contacting. For example, a pipette or similar device can be used to withdraw a predetermined amount of fluid sample from a reaction mixture, and to apply the fluid sample on the sorbent. A multiple-tipped pipette, which is used to deliver liquid reagents to standard 96-well microtiter plates, can be used to transfer fluid samples, either manually or automatically, from multiple reaction mixtures simultaneously. Because the volume of each fluid sample is small—a few microliters, say—fluid samples from numerous reaction mixtures can be applied to discrete locations on a sorbent layer, similar to "spotting" on TLC plates.

The choice of sorbent depends on the nature of the trapped component, including the component's size, polarity, charge, solubility in the fluid sample, and chemical structure. Useful sorbents generally include finely divided or microporous adsorbents used in solid phase extraction (SPE), liquid chromatography (adsorption and ionic exchange chromatography), and TLC. These materials include, but are not limited to, silica—with or without a bonded phase—activated alumina, magnesium silicate, graphitized carbon, dextran, agarose, cellulose, methacrylate, polystyrene, and divinylbenzene-polystyrene copolymer. Typical groups that comprise the silica bonded phase include butyldimethyl, octyl, octadecyl, cyanopropyl, diol, aminopropyl, phenyl, and phenyl polysiloxane. Other suitable sorbents include affinity chromatography media, which comprise a support matrix—cross-linked agarose, cellulose, or modified methacrylate, for instance—and ligands linked to the matrix. The ligands exhibit specific and reversible binding affinity for the trapped component. In some cases, spacer arms link small ligands to the matrix to improve bonding with the trapped component.

Trapping 16 can occur through physical adsorption, chemisorption, absorption, or chemical bonding. The trapping mechanism depends on the chemical structure of the sorbent and the component, and can strongly influence the detecting 18 step. For example, certain detection techniques, such as gas chromatography, mass spectroscopy, and liquid chromatography, require the release of the component from the sorbent. Such detection techniques would preclude the use of a sorbent that, for example, irreversibly bonds to the component. Furthermore, choosing a sorbent that is highly selective for the component can improve the accuracy of the detecting 18 step by reducing interference from other constituents of the fluid sample.

The detecting 18 step may be quantitative, yielding an absolute measure of the amount of the trapped component. By repeating the contacting 14 step, the trapping 16 step, and the detecting 18 step during the course of reaction, one may determine rates of reaction from changes in the amount of the trapped component with time. Instead of quantitative data, the detecting 18 step may provide qualitative data, which one can use to rank reaction mixtures 12.

In many cases, the component or components are detected while trapped on the sorbent. In one approach, the trapped component is detected by absorption spectroscopy, which involves measuring the absorption of radiant energy by the trapped component. Absorption can occur throughout the electromagnetic spectrum, ranging from the gamma region (nuclear resonance absorption) to the radio region (nuclear magnetic resonance), though generally absorption spectroscopy is performed in the ultraviolet, visible, and infrared regions of the electromagnetic spectrum. Through appropriate calibration, the absorption spectrum can be used to quantify the amount of the component trapped on the sorbent.

In another approach, the sorbent is exposed to one or more indicator reagents to obtain a characteristic change in appearance of the sorbent resulting from an interaction or reaction of the indicator reagent with the trapped sorbent. Changes in appearance of the sorbent include changes in color that are visible to the eye or changes in fluoresence when the sorbent is exposed to ultraviolet light. Suitable indicator reagents (stains) include those used to visualize TLC spots. Without wanting to be limited, Table 1 lists some useful reagents for detecting various classes of components sampled from the reactions mixtures 12.

TABLE 1

Indicator Reagents for Detection of Reaction Mixture Components.

| Component Class | Indicator Reagent |
|---|---|
| Acetylene | Dicobalt octacarbonyl |
| Acid, organic | Bromocresol green |
| | Bromocresol green-bromophenol blue-potassium permanganate |
| | Bromocresol purple |
| | Glucose-Aniline |
| Acid, organic aromatic | Hydrogen Peroxide |
| Alcohols, higher, phenols | Vanillin-sulphuric acid |
| Aldehydes, Ketones | o-Diansidine |
| | 4-Amino-5-hydrazino-1,2,4-triazole-3-thiol |
| | biphenyl-2-amine |
| | 2,4-Dinitrophenyhydrazine |
| | Malachite green |
| | Phosphomolybdic acid |
| Amides | Chlorine-pyrazolinone-cyanide |
| | Hydroxylamine-ferric chloride |
| Amines, aliphatic | Nitroprusside(sodium)-acetaldehyde |
| | Nitroprusside(sodium)-ferricyanide |
| | 1-Naphthaleneacetic anhydride |
| Amines, primary | Ninhydrin |
| | Fluorescamine |
| Amines, secondary | Dansyl chloride |
| Amines, aromatic | Sodium nitrite-HCl-a-naphthol |
| | 5-Chloro-4,6-dinitrobenzofuran |
| | 2,6-dibromo-4-quinonechlorimine (Gibb's Reagent) |
| Amino acids | 2,4-Dinitrofluorobenzene |
| | Isatin-zinc acetate |
| Anhydrides | Hydroxylamine-ferric chloride |
| Coumarins | Cupric sulphate-citrate |

TABLE 1-continued

Indicator Reagents for Detection of Reaction Mixture Components.

| Component Class | Indicator Reagent |
|---|---|
| 1,2-Diols | Lead tetraacetate |
| | Lead tetraacetate-rosaniline |
| Disulphides | Nitroprusside (sodium) |
| Esters | Hydroxylamine-ferric chloride |
| Heterocycles, N-containing | 4-Methylumbelliferone |
| | Tetracyanoethylene |
| Indole and derivatives | Cinnamaldehyde-HCl |
| | 4-Dimethylaminobenzaldehyde-HCl |
| | 4-Dimethylaminocinnamaldehyde |
| | Ferric chloride-perchloric acid |
| | Ferric chloride-sulphuric acid |
| Keto acids | o-Phenylenediamine-trichloroacetic acid |
| Ketones, methyl | Nitroprusside(sodium)-NaOH |
| Lactones | Hydroxylamine-ferric chloride |
| Mercaptans | Nitroprusside(sodium) |
| Quaternary ammonium salts | Dragendorff's reagent |
| Oximes | Cupric chloride |
| Phthalate esters | Resorcinol-zinc chloride-sulphuric acid |
| Polyalcohols | Silver nitrate-sodium hydroxide |
| | Potassium permanganate |
| | Metaperiodate(sodium)-benzidine |
| Polyethylene glycols and derivatives | Iodine-sulphuric acid |
| Polyphenols | Stannic chloride |
| Polyphenyls | Cerium sulphate-nitric acid |
| Pyridine compounds | Chlorine-pyrazolinone-cyanide |
| | Bromine cyanide-4-aminobenzoic acid |
| Pyrimidines, barbiturates | Fluorescein-ammonia |
| Sulphonic acid, alkyl and aryl | Pinacryptol yellow |
| | Silver nitrate-fluorescein |
| Terpenes | Antimony chloride |
| Urea and derivatives | Nitroprusside(sodium)-hydrogen peroxide |
| Xanthine derivatives | Ferric chloride-iodine |

For screening purposes, a visual comparison of stained sorbents is often sufficient to rank reaction mixtures. But, the use of indicator reagents along with devices for measuring color intensity—a charged couple device (CCD) camera or a spectrum analyzer, for example—can provide accurate quantitative as well as precise qualitative information about the reaction mixtures 12. Thus, a CCD camera, for instance, can distinguish between sorbent stains that appear similar to the unaided eye. Through proper calibration with standards, the CCD camera can also yield an absolute measure of the amount of the trapped component on the sorbent. One can use the quantitative data to calculate conversion, rates of reaction, catalyst selectivity, and the like. When the sorbent is in contact with the reaction mixture during the course of the reaction, imaging can be done in real time, e.g., through the back of the plate.

As mentioned above, gas chromatography, liquid chromatography, and mass spectroscopy, can be used in the detecting 18 step, but require removal of the trapped component from the sorbent (absorption spectroscopy, including nuclear magnetic resonance spectroscopy, can also be used to detect the component after removal from the sorbent). The method for removing the trapped component depends on the nature of the trapping mechanism, but typically includes heating the sorbent (thermal desorption) or washing the sorbent with a solvent, or a combination of thermal desorption and solvent washing. The solvent can be a gas or a liquid, and should exhibit a greater affinity for the trapped component than the sorbent at the removal temperature.

Although the disclosed method can be used to study a broad range of gas and liquid-phase reactions, it is especially useful for screening catalyst libraries. Unless otherwise clear from its context, the term "catalyst" is used to mean any substance that enhances the rate of reaction. Catalyst is interchangeably to refer to metal complexes or pre-catalysts before activation, and to active catalyst species themselves. Also, the catalyst may not be an isolated complex, but instead may be a mixture of a ligand with a metal. In such cases, the ligand may be obtained from a ligand library, and later mixed with a metal or metal precursor to cause catalysis. Thus, library members can be ligands, which are not catalysts themselves, but must be at least mixed with a metal or metal precursor; library members can also be metal-ligand complexes, mixtures of ligands and metals or metal precursors, and the like. Catalysts or library members may also be heterogeneous catalysts, which may include, but are not limited to metals, metal oxides, mixed metal oxides, metal sulfides, metal nitrides, metal halides, metal carbides and combinations thereof.

The disclosed method of FIG. 1 can be readily applied to screening catalyst libraries made by parallel synthesis. Each library member is combined with one or more reactants to form the reaction mixtures 12. Each of the reaction mixtures 12 can further include one or more solvents, activators, and other additives needed for reaction. In an initial or primary screen, each of the reaction mixtures usually differ only in the catalyst used. Once the primary screen identifies a set of leads or promising catalysts, the reaction mixtures and conditions can be varied in a secondary screen to further characterize the promising members of the catalyst library.

During or after reaction, fluid samples from each of the reaction mixtures 12 are contacted with a sorbent in order to trap at least one component of the fluid samples, which is typically a desired reaction product. Following the contacting 14 and the trapping 16 steps, the trapped component or components are detected by the methods described earlier. These methods include, but are not limited to: direct absorption spectroscopy of the trapped component; staining the sorbent with an indicator reagent followed by fluorescence detection or colorimetric analysis; and removal of the component from the sorbent, followed by quantification using liquid chromatography, gas chromatography or mass spectroscopy.

FIG. 2–FIG. 6 show useful devices for carrying out the disclosed method. Although many of the devices are described in terms of screening libraries of catalysts, the various devices can be used to analyze a broad spectrum of reaction mixtures.

Figure 2:
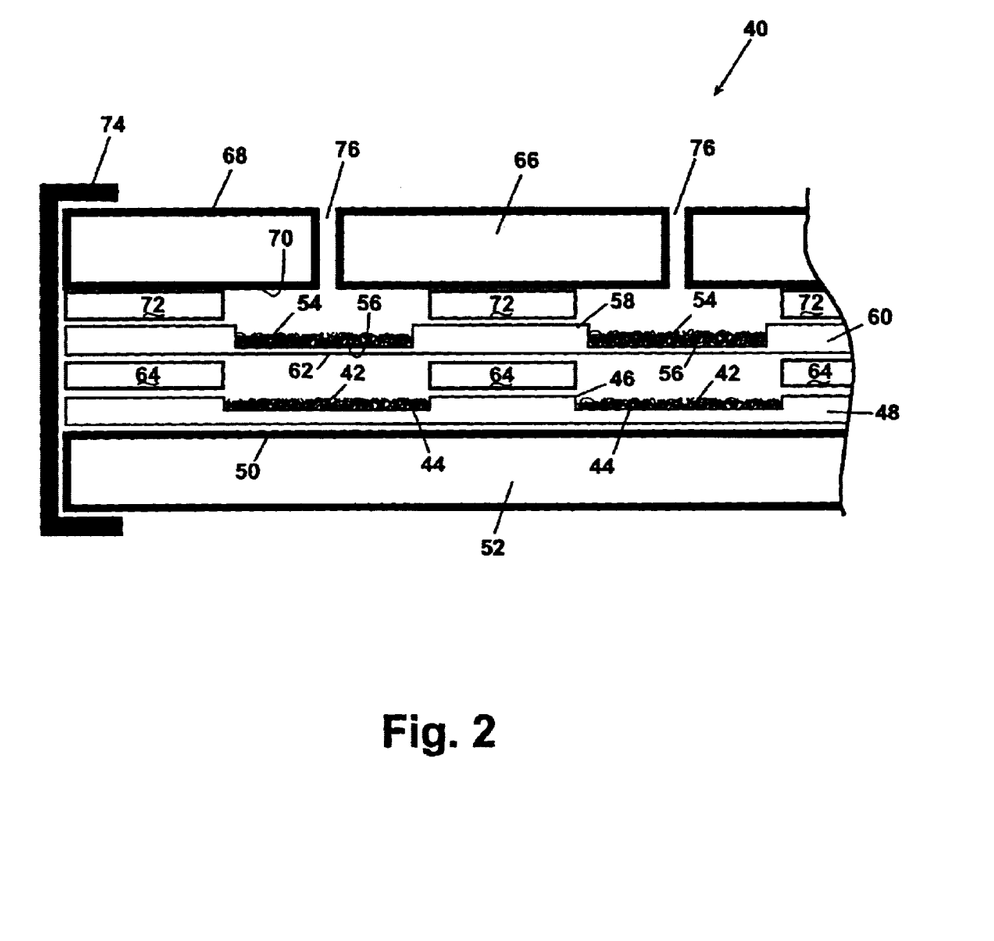
FIG. 2 shows a cross-sectional view of a portion of an apparatus that can be used to screen catalyst library members arrayed on a wafer.

FIG. 2 shows a cross-sectional view of a portion of an apparatus 40 that can be used to screen catalyst library members 42. The library members 42, along with other condensed-phase constituents of the reaction mixtures, are deposited in depressions 44 formed along an upper surface 46 of a planar substrate or wafer 48. A lower surface 50 of the wafer 48 is disposed on a heating block 52. Porous sorbent 54 is deposited in depressions 56 formed along an upper surface 58 of a gas permeable solid layer 60. Alternatively, the sorbent can be deposited in depressions formed along a lower surface 62 of the gas permeable solid layer, or can comprise a continuous layer supported on either the upper surface 58 or the lower surface 62 of the gas permeable solid layer 60. The gas permeable solid layer 60 can comprise any inert, porous material, including glass, metal or polymer frits, quartz paper, or wire mesh. Examples of polymer frits include those made from polyethylene or polytetrafluoroethylene (PTFE); "inert" means the material is chemically resistant to the specific reaction mixtures it may contact during use. One may dispense with the gas permeable solid layer 60 if the sorbent can be formed into a dimensionally stable layer.

As shown in FIG. 2, the gas permeable solid layer 60 is positioned above the wafer 48. An optional first gasket 64, which can be any inert, resilient material, provides stress relief, and helps prevent migration of reaction mixture components between library members 42. A cover 66, having an upper surface 68 and a lower surface 70 is disposed above the upper surface 58 of the gas permeable solid layer 60. An optional second gasket 72 is sandwiched between the lower surface 70 of the cover 66, and the upper surface 58 of the gas permeable solid layer 60. Like the first gasket 64, the second gasket 72 can be any inert, resilient material, provides stress relief, and helps prevent cross contamination of reaction mixtures. Clamps 74 or similar compressive fasteners holds the various parts of the apparatus 40 in place.

Passageways 76 are formed in the cover 66 that extend from the lower 70 to the upper 68 surfaces of the cover 66 and provide flow paths for vapor phase components of the reaction mixtures. Thus, during screening, one or more gaseous reactants enter the apparatus 40 through the passageways 76, flow through the sorbent 54 and contact the library members 42 where they react. The heating block 52 provides thermal energy, if needed to drive the reactions, and is either surrounded by a temperature-controlled heating blanket or immersed in a temperature-regulated bath. Alternatively, the heating block 52 can contain heating elements and temperature sensing devices—thermocouples (TC), thermistors, resistance thermometric devices (RTD), and the like—that communicate with a processor (not shown) that maintains the temperature of each of the library members 42 at one or more pre-selected values. Reaction products diffuse away from the library members 42 and contact the sorbent 54, which selectively traps one or more reaction products of interest. After the reactions are complete, one measures the relative or absolute amount of the trapped component in accordance with the detecting 18 step of FIG. 1.

Figure 3:
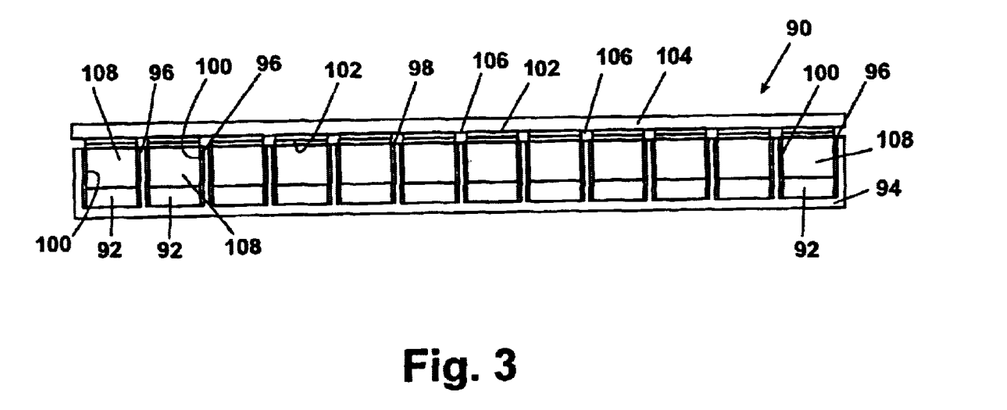
FIG. 3 shows a cross-sectional view of an apparatus that can be used to analyze liquid-phase reaction mixtures.

FIG. 3 shows a cross-sectional view of an apparatus 90 that can be used to analyze liquid-phase reaction mixtures 92. The apparatus comprises a reaction block 94 having wells 96 formed along an upper surface 98 for containing the reaction mixtures 92. Optionally, each of the wells 96 can contain a removable lining 100—such as a glass insert—so that the reaction mixtures 92 can be easily removed from the reaction block 94. A sorbent layer 102 is disposed above the upper surface 98 of the reaction block 94 such that the wells 96 (or removable lining 100) and the sorbent layer 102 define vessels for containing the reaction mixtures 92. Typically, the reaction block 94 contains heating elements and temperature sensing devices—TCs, thermistors, RTDs, and the like—that communicate with a processor (not shown). The heating elements, temperature sensing devices, and the processor comprise a temperature control system that maintains the temperature of each of the reaction mixtures 92 at one or more pre-selected values. Alternatively, the reaction block 94 can be surrounded by a temperature-controlled heating blanket or immersed in a temperature-regulated bath.

The sorbent layer 102 shown in FIG. 3 is supported on a solid layer 104 though one may dispense with the solid layer 104 if the sorbent layer 102 is dimensionally stable and has the requisite mechanical strength. In addition, the sorbant layer 102 shown in FIG. 3 is discontinuous: regions 106 exist along the solid layer 104 that lack sorbent. These bare regions 106, which are located between the wells 96, help prevent cross contamination of reaction mixtures 92, and can be formed by bead blasting a TLC plate.

Vapor from the reaction mixtures 92 fills the headspace 108 of each of the wells 96. During and/or following reaction, the vapor contacts the sorbent layer 102, trapping the component of interest. One can then measure the relative or absolute amount of the trapped component in accordance with the detecting 18 step of FIG. 1. As discussed above, the fraction of the component of interest in the vapor phase is generally different than the fraction of the same component in the liquid phase, which may lead to difficulties in comparing data among reaction mixtures. To minimize this problem, the reaction mixtures 92 are usually completely vaporized at the conclusion of reaction by heating the reaction block 94 thereby trapping a substantial amount of the component of interest.

Figure 4:
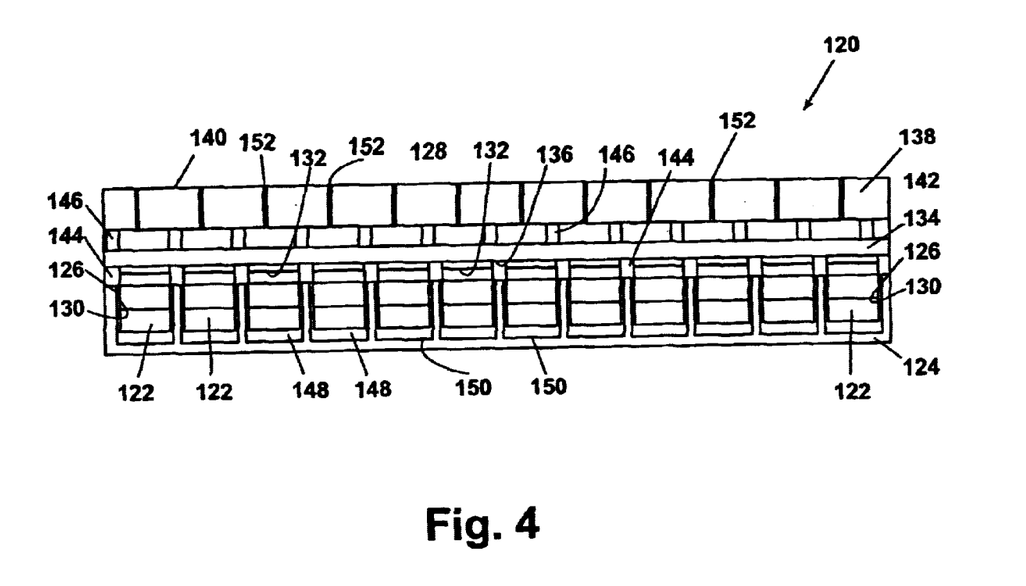
FIG. 4 shows a cross-sectional view of an apparatus that can be used to analyze reaction mixtures, especially those comprising catalyst library members.

FIG. 4 shows a cross-sectional view of another apparatus 120 that can be used to analyze reaction mixtures, especially those comprising catalyst library members 122. Like the apparatus 90 shown in FIG. 3, it comprises a reaction block 124 having wells 126 formed along an upper surface 128 for containing the catalysts 122. Each of the wells 126 shown in FIG. 4 contain an optional removable lining 130, a glass insert, for example, so that the catalyst library members 122 can be easily removed from the reaction block 124. A sorbant layer 132 is disposed above the upper surface 128 of the reaction block 124 such that the wells 126 (or removable lining 130) and the sorbent layer 132 define vessels for containing the catalyst library members 122. Typically, the reaction block 124 contains heating elements and temperature sensing devices—TCs, thermistors, RTDs, and the like-that communicate with a processor (not shown). The heating elements, temperature sensing devices, and the processor comprise a temperature control system that maintains the temperature of each of the catalyst library members 122 at one or more pre-selected values. Alternatively, the reaction block 124 can be surrounded by a temperature-controlled heating blanket or immersed in a temperature-regulated bath.

The sorbent layer 132 shown in FIG. 4 is supported on an optional, gas permeable solid layer 134, and is discontinuous. As mentioned when describing FIG. 3, these bare regions 136, which are located between the wells 126, help prevent migration of gas-phase reaction mixture components between adjacent catalyst library members 122, and can be formed by bead blasting a TLC plate.

The apparatus 120 further comprises a cover 138 having an upper surface 140 and a lower surface 142, which is disposed above the solid layer 134. Optional first 144 and second 146 gaskets, are sandwiched between the gas permeable solid layer 134 and either the upper surface 128 of the reaction block 124 or the lower surface 142 of the cover 138, respectively. The gaskets 144, 146, which can be made of any inert, resilient material, provide stress relief, and help prevent migration of reaction mixture components between catalyst library members 122. In addition, resilient spacers 148, located at the bottom 150 of each of the wells 126, prevent damage to the removable lining 130 due to compressive forces exerted by fasteners (not shown) used to seal the apparatus 120.

Passageways 152 formed in the cover 138 extend from the upper 140 to the lower 142 surfaces of the cover 138 and provide flow paths for vapor phase components of the reaction mixtures. Thus, when screening catalyst library members 122, one or more gaseous reactants enter the apparatus 120 through the passageways 152, flow through the gas permeable solid layer 134 and porous sorbent layer 132 and contact catalyst library members 122. Heating elements within the reaction block 124 provide thermal energy, if needed, to drive the reactions. Reaction products diffuse away from the library members 122 and contact the sorbent layer 132, which selectively traps one or more reaction products of interest. After the reactions are complete, one measures the relative or absolute amount of the trapped component in accordance with the detecting 18 step of FIG. 1.

Figure 5:
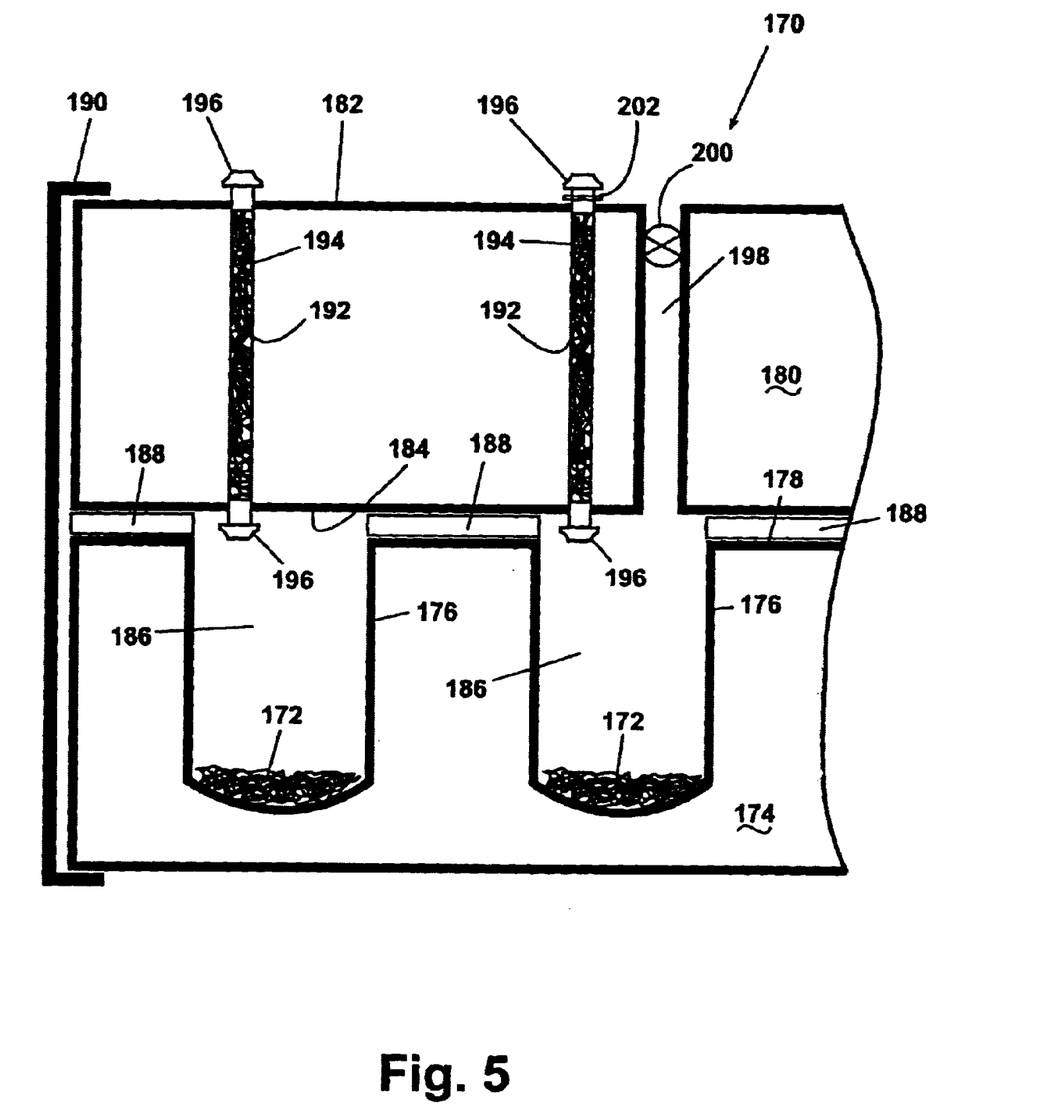
FIG. 5 shows a cross-sectional view of a portion of an apparatus that can be used to screen catalyst library members with both gas-phase and liquid-phase reactants.

FIG. 5 shows a cross-sectional view of a portion of an apparatus 170 that can be used to screen catalyst library members 172 with both gas-phase and liquid-phase reactants. Like the apparatus 90, 120 shown in FIGS. 3 and 4, it comprises a reaction block 174 having wells 176 formed along an upper surface 178 for containing catalyst library members 172. Though not shown, each of the wells 176 can optionally contain a removable lining so that the catalyst library members 172 and other condensed-phase components of the reaction mixtures can be easily removed from the reaction block 174. Generally, the reaction block 174 contains heating elements and temperature sensing devices—TCs, thermistors, RTDs, and the like—that communicate with a processor (not shown). The heating elements, temperature sensing devices, and the processor comprise a temperature control system that maintains the temperature of each of the catalyst library members 172 at one or more pre-selected values. Alternatively, the reaction block 174 can be surrounded by a temperature-controlled heating blanket or immersed in a temperature-regulated bath.

The apparatus 170 further comprises a cover 180 having an upper surface 182 and a lower surface 184. The lower surface 184 of the cover 180 is disposed above the upper surface 178 of the reaction block 174, and along with the wells 176, define vessels 186 for containing the reaction mixtures. A gasket 188 is sandwiched between the reaction block 174 and the cover 180. The gasket 188, which can be made of any inert, resilient material, provides stress relief, and helps prevent migration of vapor-phase components of the reaction mixtures between vessels 186. Clamps 190 or similar compressive fasteners holds the various parts of the apparatus 170 in place.

First passageways 192 formed in the cover 180, extend from the upper surface 182 to the lower surface 184 of the cover 180, and provide flow paths for vapor phase components of the reaction mixtures. Each of the first passageways 192 contains a sorbent trap 194—a sorbent filled tube for trapping the component or components of interest.

Though component trapping can occur during reaction, screening of catalysts involved in condensed phase reactions usually undertaken after reaction is complete. In this way, one may obtain an absolute measure of the amount of a particular reaction product formed by completely vaporizing each of the reaction mixtures. During this vaporizing step, gas-phase components of the reaction mixtures exit the vessels 186 through the sorbent traps 194, which selectively entrap the desired reaction product. Because the sorbent traps 194 are located in the cover 180, the trapped component can be analyzed by separating the cover 180 from the reaction block 174. The sorbent traps can have optional fittings 196 that provide connection to an analyzer such as a liquid chromatograph, gas chromatograph, or mass spectrometer.

The apparatus 170 may further comprise second passageways 198 that are formed in the cover 180 and extend from the upper surface 182 to the lower surface 184 of the cover 180. When screening catalyst library members 172, one or more gas-phase reactants are introduced into the vessels 186 through the second passageways 198 and contact the catalyst library members 172 where they react. Gas-phase reaction products diffuse away from the catalyst library members 172, and exit the vessels 186 through the first passageways 192 and sorbent traps 194. A check valve 200 in each of the second passageways 198 prevent gas-phase components from leaving the vessels 186 through the second passageways 198, and each of the sorbent traps 194 are fitted with a flow restrictor 202 which maintains a positive gauge pressure in the vessels 186.

Figure 6:
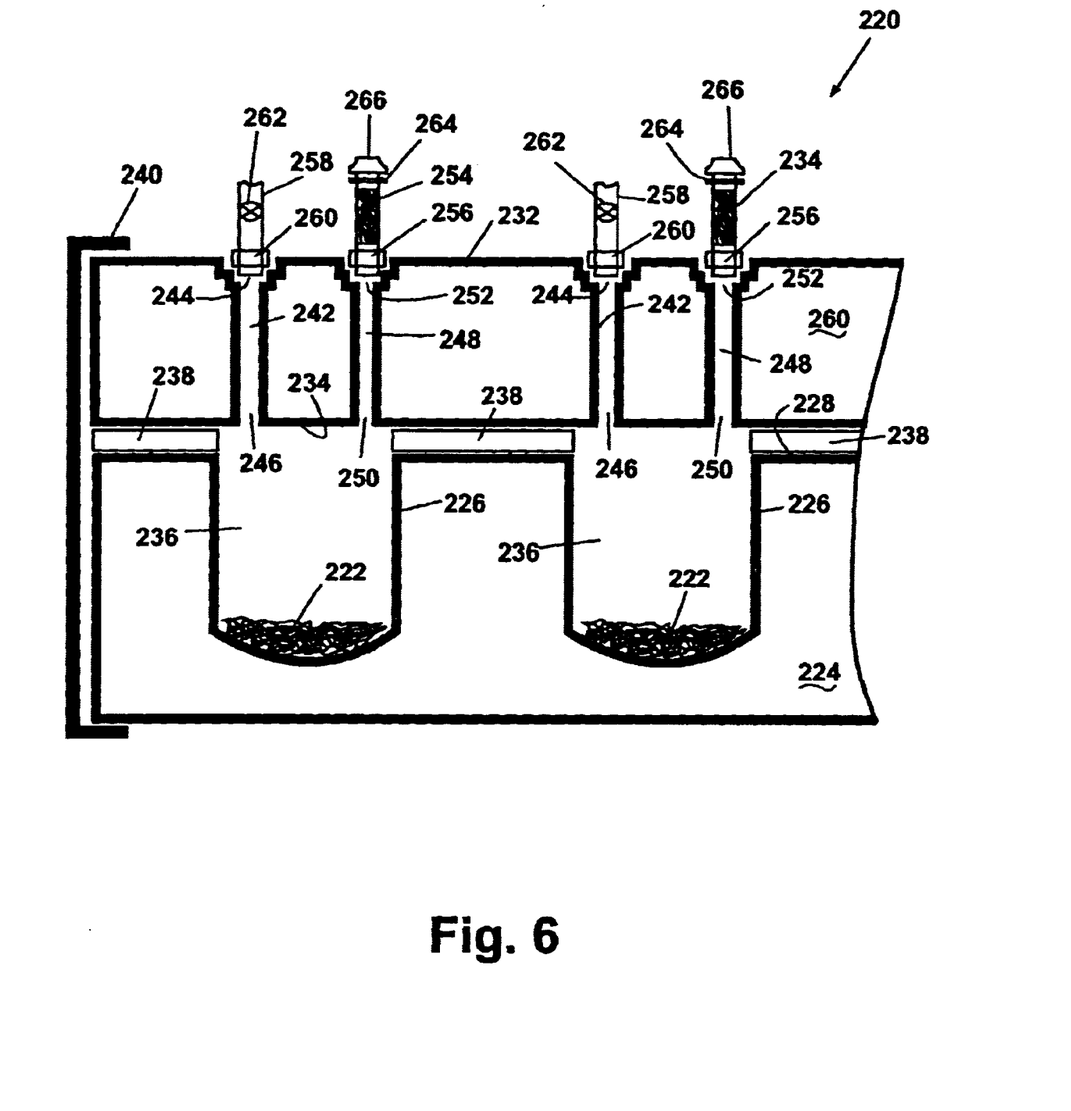
FIG. 6 shows a cross-sectional view of a portion of an apparatus that can be used to screen catalyst library members with gas-phase reactants.

Finally, FIG. 6 shows a cross-sectional view of a portion of an apparatus 220 that can be used to screen catalyst library members 222 with gas-phase reactants. Like the apparatus 170 shown in FIG. 5, the apparatus 220 comprises a reaction block 224 having wells 226 formed along an upper surface 228 for containing catalyst library members 222. Though not shown, each of the wells 226 can optionally contain a removable lining so that the catalyst library members 222 and other condensed-phase components of the reaction mixtures can be easily removed from the reaction block 224. Generally, the reaction block 224 contains heating elements and temperature sensing devices—TCs, thermistors, RTDs, and the like—that communicate with a processor (not shown). The heating elements, temperature sensing devices, and the processor comprise a temperature control system that maintains the temperature of each of the catalyst library members 222 at one or more pre-selected values. Alternatively, the reaction block 224 can be surrounded by a temperature-controlled heating blanket or immersed in a temperature-regulated bath.

The apparatus 220 further comprises a cover 230 having an upper surface 232 and a lower surface 234. The lower surface 234 of the cover 230 is disposed above the upper surface 228 of the reaction block 224, and along with the wells 226, define vessels 236 for containing the reaction mixtures. A gasket 238, which sandwiched between the reaction block 224 and the cover 230, can be made of any inert, resilient material; the gasket 238 provides stress relief, and helps prevent migration of vapor-phase components of the reaction mixtures between vessels 236. Clamps 240 or similar compressive fasteners holds the various parts of the apparatus 220 together.

First 242 and second 248 passageways are formed in the cover 230, and extend from the upper surface 232 to the lower surface 234 of the cover 230. The first passageways 242, whose inlets 244 and outlets 246 are located along the upper surface 232 and the lower surface 234 of the cover 230, respectively, provide flow paths for vapor phase components entering the vessels 236. The second passageways 248, whose inlets 250 and outlets 252 are located along the lower surface 234 and the upper surface 232 of the cover 230, respectively, provide flow paths for vapor phase components leaving the vessels 236. Sorbent traps 254 are attached to the outlets 252 of the second passageways 248 via connectors 256. The connectors 256 allow removal of the sorbent traps 254 after the contacting and trapping steps for remote analysis.

When screening catalyst library members 222, one or more gas-phase reactants are introduced into the vessels 236 through gas reactant feed lines 258, which are attached to the inlets 244 of the first passageways 242 using connectors 260. The gas-phase reactants contact the catalyst library members 222 and react. Gas-phase reaction products diffuse away from the catalyst library members 222, and exit the vessels 236 through the second passageways 248 and sorbent traps 254. A check valve 262 in each of the gas reactant feed lines 258 prevent gas-phase components from leaving the vessels 236 through the first passageways 242, and each of the sorbent traps 254 are fitted with a flow restrictor 264 which maintains a positive gauge pressure in the vessels 236. In addition, the sorbent traps can have optional fittings 266 that provide connection to an analyzer such as a liquid chromatograph, gas chromatograph, or mass spectrometer.

EXAMPLE

The follow example is intended as illustrative and non-limiting, and represents a specific embodiment of the present invention.

The present invention was used to study the catalytic formation of aniline. The reaction was carried out in a multi-well reactor of the type shown in FIG. 3. A catalyst comprising an oxide of nickel and zirconium along with forty microliters benzene and 10 mg of ammonium carbonate was charged to each of the wells. Ammonia and benzene were allowed to react at 300° C. for four hours. Following reaction, fluid samples from each of the reaction mixtures were contacted with a silica gel sorbent to trap aniline present in the reaction mixtures. The silica gel was supplied on a TLC plate.

Two methods were used to contact the sorbent with fluid samples from each of the reaction mixtures. In one method, 2 microliter aliquots from each of the reaction mixtures were spotted on the TLC plate using a pipette. In another method, the TLC plate was placed on the surface of the multi-well reactor. The reactor block was maintained at a temperature of 45° C. for 15 minutes, which completely vaporized (evaporated) the reaction mixtures, and allowed vapor from each of the reaction mixtures to contact discrete areas of the silica gel layer.

Figure 7:
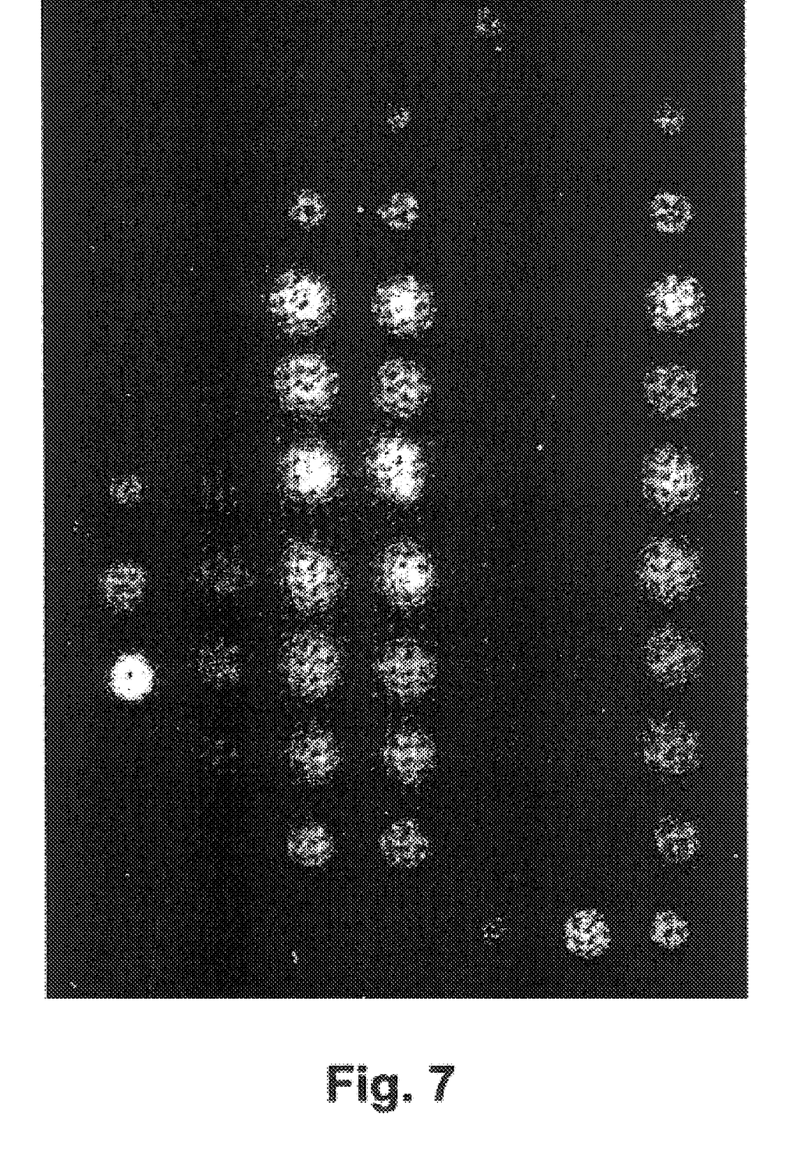
FIG. 7 is a photograph of a TLC plate spotted with 2 microliter aliquots of reaction mixtures and stained with fluorescamine.

For both contacting methods, an indicator reagent, fluorescamine (spiro[furan-2(3H), 1' (3' H')-isobenzofuran]-3,3'-dione, 4-phenyl-(9 CI) or 10-phenylspiro[2,3,3a,7a-tetrahydroindene-1,4'-cyclopentene]-10-ene) was used to detect aniline trapped on the silica gel layer. A 150 ppm solution of fluorescamine dispersed in methylene chloride was sprayed on the TLC plates using a commercially-available TLC aerosol applicator. The reaction between aniline and fluorescamine occurred in about twenty seconds at room temperature. The fluorescent product formed had a persistent fluorescence that was detected using long wavelength ultraviolet excitation energy (390 nm); the resulting fluorescence signal (490 nm) was passed through a blue-green filter and collected using a CCD camera. A photograph of the TLC plate spotted with 2 microliter aliquots of the reaction mixtures and stained with fluorescamine is shown in FIG. 7.

Figure 8:
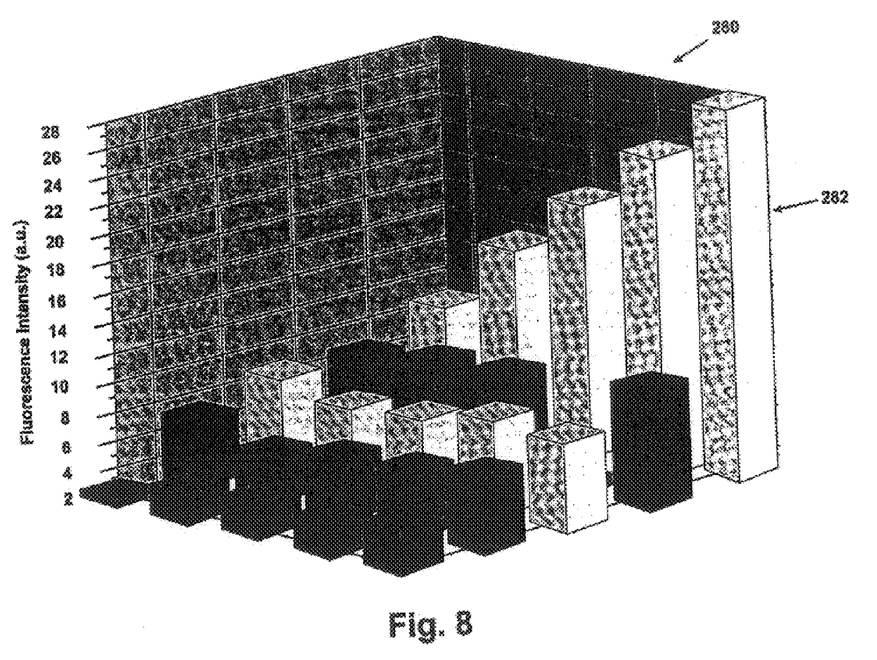
FIG. 8 shows a typical bar plot of integrated fluorescence intensity of spots on a TLC plate.

The fluorescent spots on the TLC plates were numerically integrated; a typical bar plot 280 of the integration data are shown in FIG. 8. Integrated fluorescence intensity for aniline standards trapped on the TLC plate along with aniline from the reaction mixtures is shown in the back row 282 of FIG. 8. Although the amount of aniline in the standards was apparently greater than the amount of aniline present in the reaction mixtures, normally the standards could be used to relate the fluorescence intensity to amount of aniline in the reaction mixtures.

Figure 9:
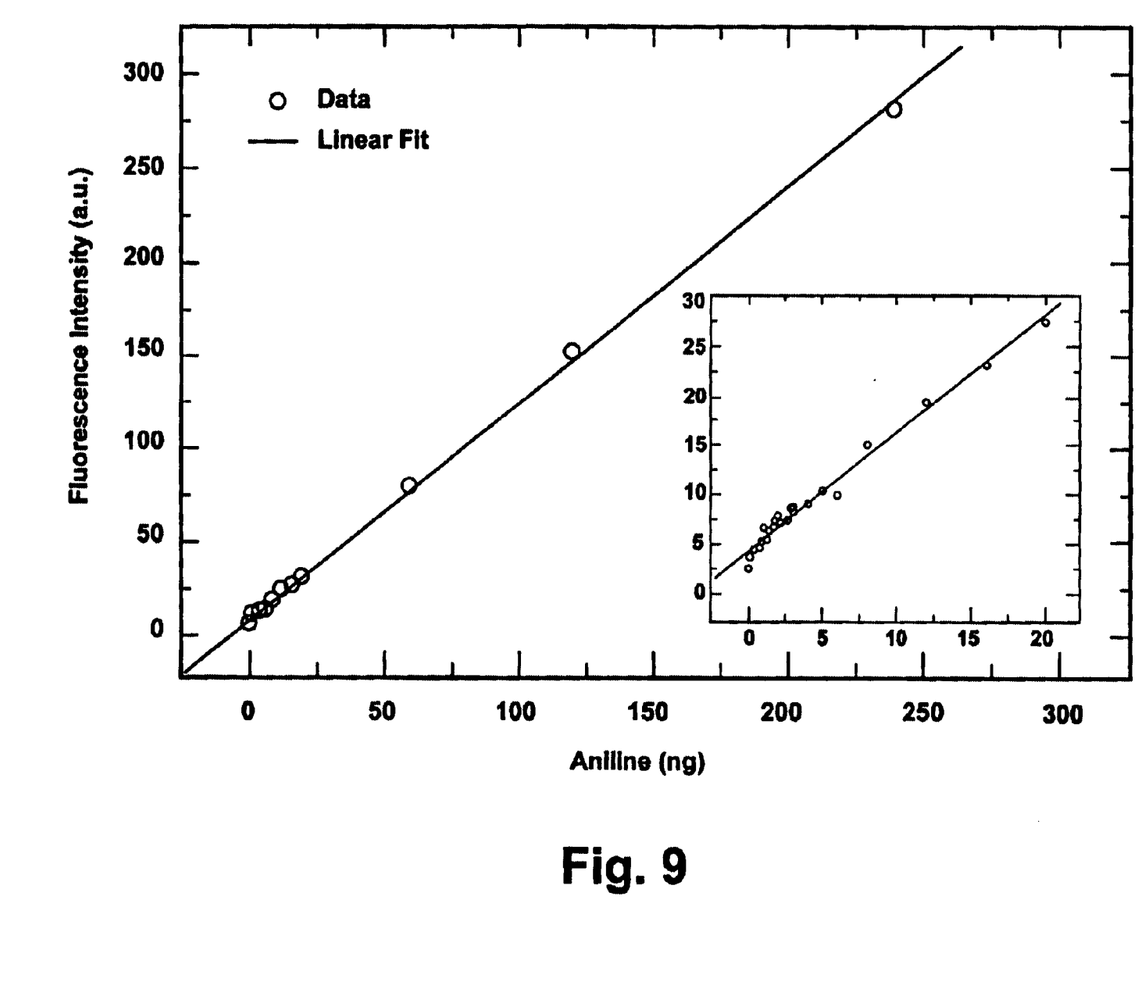
FIG. 9 shows a plot of fluorescence intensity of an aniline-fluorescamine product versus the amount of aniline.

In a separate experiment, aniline standards were applied to a TLC plate and detected in a manner identical to the reaction mixtures. Integration of the fluorescence signal from the standards indicates that the method is capable of detecting on the order of 0.5 ng of aniline, and that the linear dynamic range for detection extends over three orders of magnitude. See FIG. 9. Since fluorescamine is not fluorescent, it can be applied in large excess without interfering with the detection of aniline.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An apparatus for analyzing reaction mixtures comprising:
    a reaction block having wells formed along an upper surface; and
    a sorbent layer disposed above the upper surface of the reaction block such that the wells and the sorbent layer define vessels for containing the reaction mixtures;
    wherein the sorbent layer is adapted to selectively trap at least one fluid component of the reaction mixtures.

2. The apparatus of claim 1, wherein the reaction block further comprises a system for regulating temperature of the reaction mixtures.

3. The apparatus of claim 1, wherein the reaction block further comprises heating elements.

4. The apparatus of claim 1, wherein the wells each contain a removable lining.

5. The apparatus of claim 1, wherein the sorbent layer is supported on a solid layer.

6. The apparatus of claim 5, wherein the sorbent layer and the solid layer comprise a thin layer chromatography plate.

7. The apparatus of claim 5, wherein the solid layer is gas permeable.

8. The apparatus of claim 7, further comprising a cover having an upper surface and a lower surface, the lower surface of the cover disposed above the solid layer; and
    a plurality of conduits formed in the cover that provide passageways for vapor flow between each of the vessels and the upper surface of the cover.

9. An apparatus for analyzing reaction mixtures comprising:
    vessels for containing each of the reaction mixtures; and
    sorbent traps in fluid communication with the vessels via conduits;
    wherein the sorbent traps are adapted to selectively trap at least one fluid component of reaction mixtures.

10. The apparatus of claim 9, further comprising:
    a reaction block having wells formed along an upper surface; and
    a cover having an upper surface and a lower surface;
    wherein the cover is disposed above the upper surface of the reaction block such that the wells and the lower surface of the cover define the vessels for containing each of the reaction mixtures.

11. The apparatus of claim 10, wherein each of the vessels contain a removable.

12. The apparatus of claim 10, wherein the sorbent traps are located in the vessels adjacent to the lower surface of the cover.

13. The apparatus of claim 10, further comprising passageways formed in the cover that extend from the lower surface of the cover to the upper surface of the cover.

14. The apparatus of claim 12, the sorbent traps are located in at least some of the passageways.

15. The apparatus of claim 13, wherein the passageways further comprise inlet passageways and outlet passageways, wherein the outlet passageways contain the sorbent traps and the inlet passageways are adapted to provide a component of the reaction mixtures to each of the vessels.

16. The apparatus of claim 13, wherein the sorbent traps are located external to the cover and communicate with the vessels through the passageways.

17. The apparatus of claim 13, wherein the passageways further comprise inlet passageways and outlet passageways, wherein the sorbent traps communicate with the vessels through the outlet passageways, and the inlet passageways are adapted to provide a component of the reaction mixtures to each of the vessels.

18. The apparatus of claim 9, further comprising heating elements in thermal contact with the vessels.

19. The apparatus of claim 9, further comprising a temperature control system for regulating the temperature of the reaction mixtures.

20. An apparatus for screening reaction mixtures, wherein at least one constituent of the reaction mixtures is contained in depressions located along a top surface of a planar substrate, the apparatus comprising:
    a heating block adapted to support the planar substrate and to provide thermal contact with a bottom surface of the planar substrate;
    a gas permeable sorbent layer having an upper surface and a lower surface, wherein the lower surface of the sorbent layer is disposed above the top surface of the planar substrate, and the sorbent layer is adapted to selectively trap at least one vapor phase component of the reaction mixtures;
    a cover having an upper surface and a lower surface, the lower surface of the cover disposed above the upper surface of the sorbent layer; and
    passageways formed in the cover that extend from the lower surface of the cover to the upper surface of the cover and provide flow paths for vapor phase components of the reaction mixtures from the upper surface of the cover to the at least one constituent of the reactive mixture.

21. The apparatus of claim 20, wherein the heating block further comprises a system for regulating temperature of the reaction mixtures.

22. The apparatus of claims 20, further comprising a gas permeable solid layer having an upper surface and a lower surface, wherein the sorbent layer is supported on a surface selected from the group consisting of the upper surface of the gas permeable solid layer and the lower surface of the gas permeable solid layer.

23. The apparatus of claim 22, wherein the solid layer is a frit, quartz paper, or a wire.

24. The apparatus of claim 23, wherein the frit is made of glass, polyethylene, or polytetrafluoroetylene.

25. The apparatus of claim 22, wherein the sorbent layer is discontinuous.

26. The apparatus of claim 25, wherein the sorbent layer is disposed in depressions formed along a surface selected from the group consisting of the upper surface of the gas permeable solid layer and the lower surface of the gas permeable solid layer.

27. An apparatus for analyzing reaction mixtures, the apparatus comprising a reaction block comprising a plurality of reaction vessels for containing reaction mixtures, a plurality of inlet passageways, each of the inlet passageways providing a flow path for introducing one or more gas-phase reactants into one of the plurality of reaction vessels, a plurality of outlet passageways, each of the outlet passageways providing a flow path for discharging a gas-phase reaction product from one of the plurality of reaction vessels, and a plurality of sorbent traps, each of the sorbent traps being in fluid communication with one of the plurality of reaction vessels through its associated outlet passageway, and being adapted to selectively trap at least one gas-phase reaction product.

28. The apparatus of claim 27, wherein the reaction block comprises a plurality of wells formed along a surface substrate, and a cover disposed such that the wells and the cover define the plurality of reaction vessels.

29. The apparatus of claim 28 wherein the inlet and outlet passageways are formed in the cover.

30. The apparatus of claim 28 wherein the inlet and outlet passageways are formed in the cover, and extend from the upper surface to the lower surface of the cover.

31. The apparatus of claim 28 wherein the sorbent traps are located external to the cover.

32. The apparatus of claim 28 further comprising a gasket between the surface of the well-containing substrate and the cover for helping to prevent migration of vapor-phase components of the reaction mixtures between reaction vessels.

33. The apparatus of claim 29 wherein the plurality of sorbent traps are removable for remote analysis after trapping the at least one gas-phase reaction product.

* * * * *

UNITED STATES PATENT AND TRADEMARK OFFICE
CERTIFICATE OF CORRECTION

PATENT NO. : 6,667,009 B1
DATED : December 23, 2003
INVENTOR(S) : Desrosiers et al.

It is certified that error appears in the above-identified patent and that said Letters Patent is hereby corrected as shown below:

Column 13,
Line 45, delete the dash between the words "between" and "each"
Line 64, insert -- lining -- between "removable" and "."

Column 14,
Line 56, insert -- mesh -- between "wire" and "."
Line 58, delete "polytetrafluoroetylene" and insert -- polytetrafluoroethylene --

Column 16,
Line 1, insert -- of a -- before "substrate"

Signed and Sealed this

Fourth Day of May, 2004

JON W. DUDAS
*Acting Director of the United States Patent and Trademark Office*